(12) United States Patent
Li et al.

(10) Patent No.: US 11,059,854 B2
(45) Date of Patent: Jul. 13, 2021

(54) METHOD FOR PREPARING STEROID DERIVATIVE FXR AGONIST

(71) Applicant: Chia Tai Tianqing Pharmaceutical Group Co., Ltd., Lianyungang (CN)

(72) Inventors: Xiaolin Li, Shanghai (CN); Hualing Xiao, Shanghai (CN); Peng Li, Shanghai (CN); Haiying He, Shanghai (CN); Fei Hao, Shanghai (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/633,122

(22) PCT Filed: Jul. 26, 2018

(86) PCT No.: PCT/CN2018/097158
§ 371 (c)(1),
(2) Date: Jan. 22, 2020

(87) PCT Pub. No.: WO2019/020067
PCT Pub. Date: Jan. 31, 2019

(65) Prior Publication Data
US 2020/0231622 A1  Jul. 23, 2020

(30) Foreign Application Priority Data
Jul. 26, 2017 (CN) .......................... 201710619420.1

(51) Int. Cl.
*C07J 7/00* (2006.01)
*C07J 43/00* (2006.01)

(52) U.S. Cl.
CPC .................................. *C07J 43/003* (2013.01)

(58) Field of Classification Search
CPC .............................. C07J 7/0005; C07J 43/003
See application file for complete search history.

(56) References Cited

U.S. PATENT DOCUMENTS

2019/0352328 A1* 11/2019 Zampella ................. A61P 5/38

FOREIGN PATENT DOCUMENTS

| CN | 105102425 A | 11/2015 |
|---|---|---|
| CN | 106083978 A | 11/2016 |
| CN | 106661079 A | 5/2017 |
| EP | 3660031 A1 | 6/2020 |
| WO | WO 2014/066819 A1 | 5/2014 |
| WO | WO 2016/161003 A1 | 10/2016 |
| WO | WO-2016173524 A1 * | 11/2016 ............ C07J 31/006 |
| WO | WO 2017/027396 A1 | 2/2017 |
| WO | WO 2017/053428 A1 | 3/2017 |
| WO | WO 2017/079062 A1 | 5/2017 |
| WO | WO 2017/129125 A1 | 8/2017 |
| WO | WO 2017/147137 A1 | 8/2017 |
| WO | WO 2019/020068 A1 | 1/2019 |

OTHER PUBLICATIONS

RN 1612191-84-0—Jun. 23, 2014.
International Search Report for PCT/CN2018/097158 dated Oct. 10, 2018.
D'Amore, Claudio et al., "Design, Synthesis, and Biological Evaluation of Potent Dual Agonists of Nuclear and Membrane Bile Acid Receptors" Journal of Medicinal Chemistry, 2014, pp. 937-954, vol. 57.
Supplementary European Search Report for EP 18837478 dated Mar. 11, 2021.

* cited by examiner

*Primary Examiner* — Brenda L Coleman
(74) *Attorney, Agent, or Firm* — Knobbe Martens Olson & Bear LLP

(57) ABSTRACT

The present invention falls within the field of pharmaceutical chemistry, and relates to a method for preparing a steroid derivative FXR agonist and relevant intermediates. In particular, the present invention relates to a method for preparing a compound of formula I, comprising reacting a compound of formula 8 with a compound of formula 9 to obtain a compound of formula 10, obtaining a compound of formula 11 from a reaction of the compound of formula 10, and obtaining the compound of formula I from a reaction of the compound of formula 11, as well as the intermediates used, the methods for preparing the intermediates and the use of the intermediates. The reaction conditions of the preparation method are mild, and some of the steps can convert multiple groups simultaneously, thereby effectively shortening the sequence of steps. The preparation method is suitable for industrialized production.

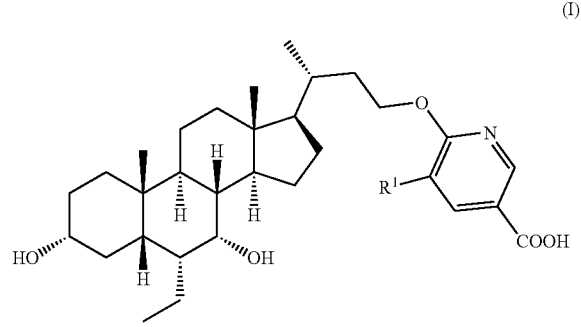

(I)

23 Claims, No Drawings

METHOD FOR PREPARING STEROID DERIVATIVE FXR AGONIST

CROSS REFERENCE TO RELATED APPLICATIONS

This application is a U.S. National Phase Application of PCT International Application Number PCT/CN2018/097158, filed on Jul. 26, 2018, designating the United States of America and published in the Chinese language, which is an International Application of and claims the benefit of priority to Chinese Patent Application No. 201710619420.1, filed on Jul. 26, 2017. The disclosures of the above-referenced applications are hereby expressly incorporated by reference in their entireties.

FIELD OF THE INVENTION

The present application belongs to the field of pharmaceutical chemistry, and in particular, the present application relates to a method for preparing a steroid derivative FXR agonist and relevant intermediates.

BACKGROUND OF THE INVENTION

Farnesoid X receptor (FXR) is an orphan nuclear receptor originally identified from rat liver cDNA libraries (B M. Forman, et al., Cell 81: 687-693 (1995)), which is closely related to insect ecdysone receptors. FXR is a member of the family of ligand-activated transcription factor nuclear receptors, including steroid, retinoid and thyroid hormone receptors (D J. Mangelsdorf, et al., Cell 83: 841-850 (1995)). It is revealed by Northern and in situ analyses that FXR is abundantly expressed in the liver, intestine, kidney, and adrenal gland (B M. Forman, et al., Cell 81: 687-693 (1995) and W. Seol, et al., Mol. Endocrinnol, 9: 72-85 (1995)). FXR forms a heterodimer with the 9-cis retinoic acid receptor (RXR), thereby binding to DNA. The FXR/RXR heterodimer preferentially binds to a component consisting of two nuclear receptor half-sites of the consensus AG(G/T)TCA, which forms inverted repeats and is separated by one nucleotide (IR-1 motif) (B M. Forman, et al., Cell 81: 687-693 (1995)). However, these compounds fail to activate FXR of mouse and human, making the natural nature of endogenous FXR ligands uncertain. Some naturally occurring cholic acids bind to and activate FXR at physiological concentrations (PCT WO 2000/37077, published on Jun. 29, 2000). As such, the cholic acids as the FXR ligands include chenodeoxycholic acid (CDCA), deoxycholic acid (DCA), lithocholic acid (LCA), and taurine and glycine conjugates of these cholic acids.

SUMMARY OF THE INVENTION

In one aspect, the application provides a method for preparing a compound of formula I,

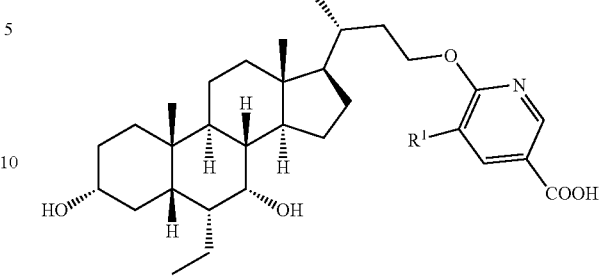

comprising the following steps:

a) reacting a compound of formula 8 with a compound of formula 9 to obtain a compound of formula 10,

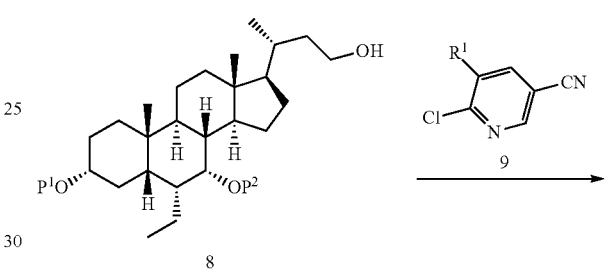

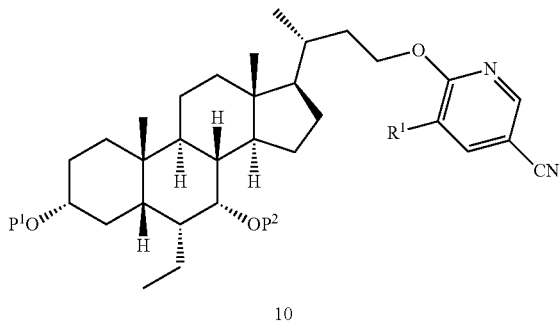

b) reacting from the compound of formula 10 to obtain a compound of formula 11,

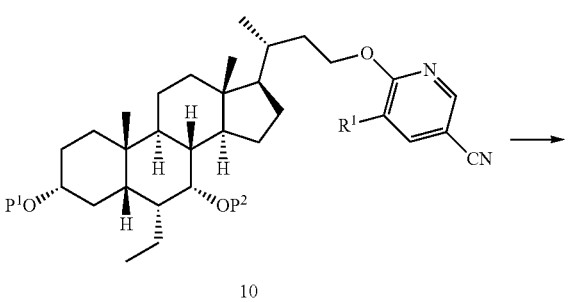

-continued

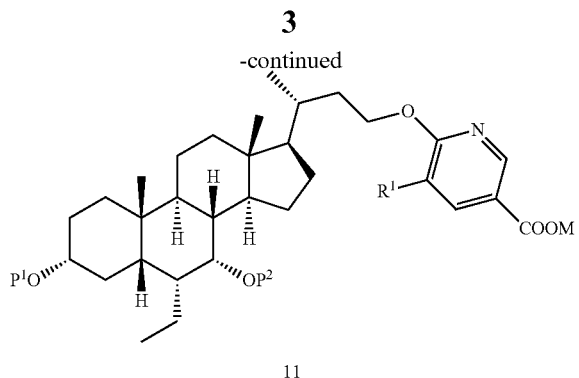

11 c) reacting from the compound of formula 11 to obtain the compound of formula I, -continued

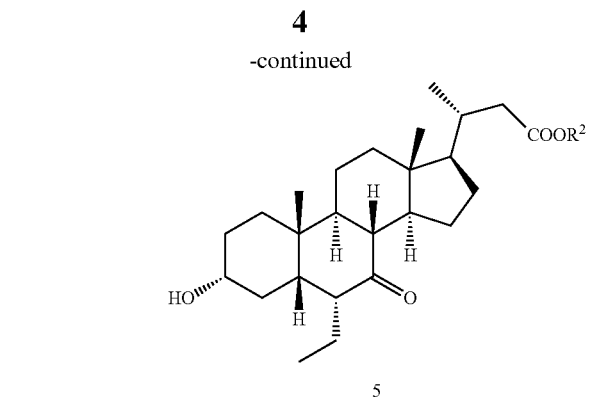

5 e) attaching a protecting group to 3-hydroxyl on the compound of formula 5 to obtain a compound of formula 6,

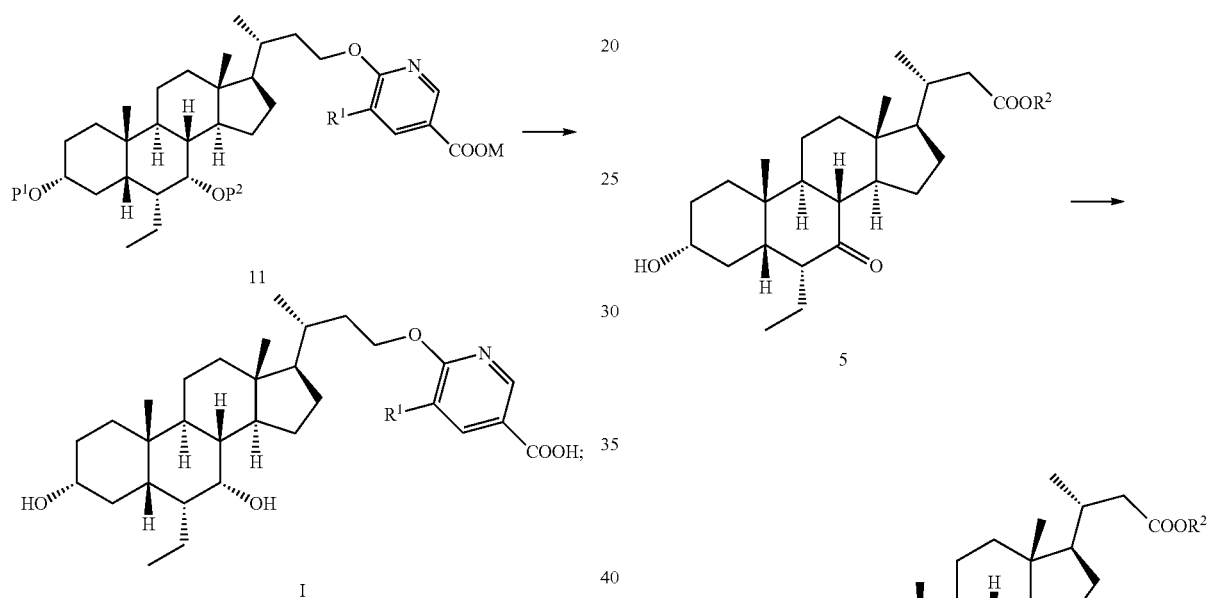

wherein, $R^1$ is selected from H, Cl, Br or F,
$P^1$ and $P^2$ are each independently selected from a hydroxy protecting group,
M is selected from a metal cation.

In another aspect, the present application provides a method for preparing the compound of formula 8, comprising the following steps:

d) subjecting a compound of formula 4 used as a starting material to an esterification reaction with an alcohol to obtain a compound of formula 5, f) reacting from the compound of formula 6 to obtain a compound of formula 7,

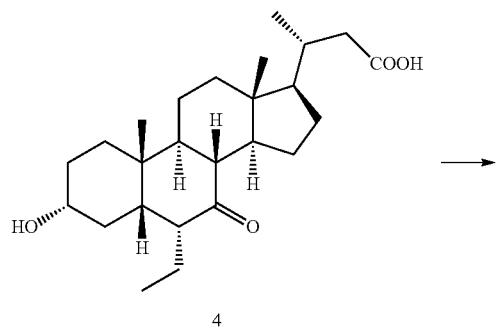

4

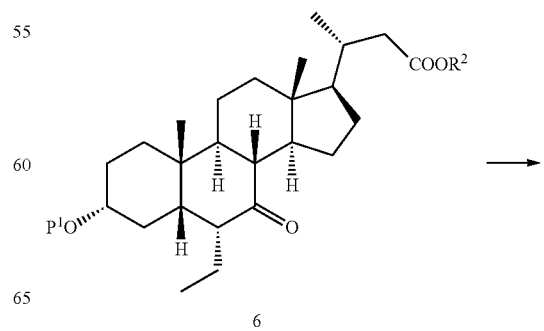

6

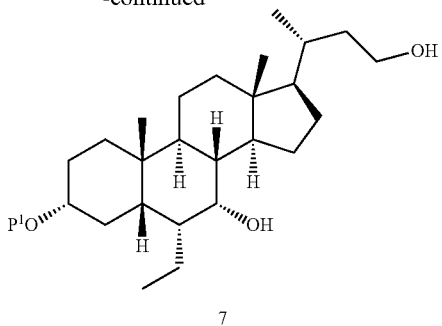

g) step g-1), attaching a protecting group P² to 7-hydroxyl and 23-hydroxyl on the compound of formula 7 to obtain a compound of formula 12; step g-2), removing 23-hydroxy protecting group P² from the compound of formula 12 to obtain the compound of formula 8,

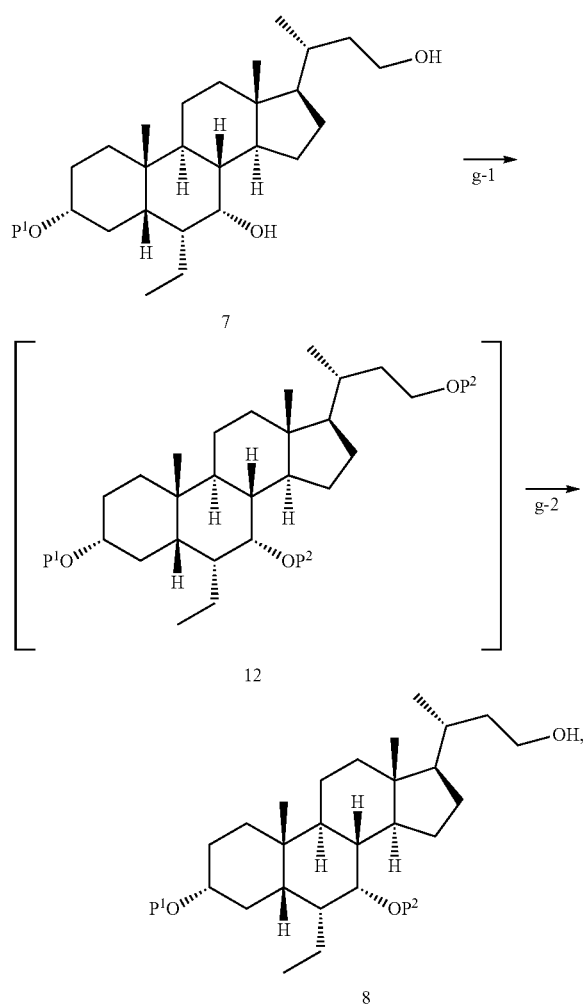

wherein, R² is selected from $C_{1-6}$ alkyl,
P¹ and P² are each independently selected from a hydroxy protecting group.

In some embodiments, said P¹ and P² are each independently selected from a hydroxy protecting group that keeps attaching to an oxygen atom at position 3 or/and at position 7 on the above steroid compound under basic condition, preferably, a hydroxy protecting group that keeps attaching to the oxygen atom at position 3 or/and at position 7 on the above steroid compound under a condition of pH≥7.5, pH≥8, pH≥8.5, pH≥9, pH≥9.5, pH≥10, pH≥10.5, pH≥11, pH≥11.5 or pH≥12.

In some embodiments, said P¹ and P² are each independently selected from a hydroxy protecting group that keeps attaching to the oxygen atom at position 3 or/and at position 7 on the above steroid compound in the presence of a base or/and a protic solvent. In some embodiments, the base is selected from a base having a pKa≥5, preferably pKa≥6, 50≥pKa≥8, 50≥pKa≥10, or 40≥pKa≥10; or the base is preferably selected from triethylamine (TEA), diisopropylethylamine (DIPEA), 1,8-diazabicycloundec-7-ene (DBU), pyridine, 2,6-dimethyl pyridine, 4-dimethylamino pyridine (DMAP), imidazole, NaOH, KOH, LiOH, $Mg(OH)_2$, $Ca(OH)_2$, NaH, KH, sodium methoxide, potassium methoxide, sodium ethoxide, potassium ethoxide, sodium t-butoxide, potassium t-butoxide, KHMDS, NaHMDS, Na, K, $KHCO_3$, $NaHCO_3$, $K_2CO_3$ or $Na_2CO_3$. In some embodiments, the protic solvent is selected from $C_{1-6}$ alcohol or water, preferably selected from isopropanol, ethanol, methanol, n-propanol, n-butanol, t-butanol or water.

In some embodiments, said P¹ is selected from a silyl ether protecting group, an alkyl ether protecting group, an alkoxymethyl ether protecting group, or an ester protecting group; preferably a trimethylsilyl (TMS), triethylsilyl (TES), t-butyldimethylsilyl (TBDMS), t-butyldiphenylsilyl (TBDPS), benzyl, p-methoxybenzyl, 3,4-dimethoxy benzyl, methyl ether, t-butyl, trityl, 4,4'-dimethoxytrityl (DMTr), methoxymethyl (MOM), benzyloxymethyl (BnOM), tetrahydrofuranyl (THP), formyl, acetyl (Ac), chloroacetyl (CAc), methoxyacetyl (MAc) or pivaloyl (Pv); more preferably trimethylsilyl (TMS), triethylsilyl (TES), t-butyldimethylsilyl (TBDMS), t-butyldiphenylsilyl (TBDPS) or methoxymethyl (MOM).

In some embodiments, said P² is selected from a silyl ether protecting group; preferably trimethylsilyl (TMS), triethylsilyl (TES), t-butyldimethylsilyl (TBDMS) or t-butyldiphenylsilyl (TBDPS); more preferably trimethylsilyl (TMS).

In some embodiments, said M is selected from an alkali metal cation or an alkaline earth metal cation; preferably $Li^+$, $Na^+$, $K^+$, $Ca^{2+}$, or $Mg^{2+}$; more preferably $Na^+$ or $K^+$.

In some embodiments, said R² is selected from $C_{1-4}$ alkyl, preferably methyl, ethyl, propyl or butyl.

In some embodiments, in step a), the reaction is carried out in the presence of a base. In some embodiments, the base is selected from a base having a pKa≥12, preferably a base having a pKa≥15, a base having 50≥pKa≥15, a base having 40≥pKa≥15 or a base having 35≥pKa≥15; or the base is preferably selected from NaOH, KOH, LiOH, NaH, KH, sodium methoxide, potassium methoxide, sodium ethoxide, potassium ethoxide, sodium t-butoxide, potassium t-butoxide, KHMDS, NaHMDS, Na or K, more preferably sodium t-butoxide, potassium tert-butoxide, KHMDS, NaHMDS, NaH, KH or Na, further preferably sodium t-butoxide or potassium t-butoxide.

In some embodiments, in step a), the solvent used in the reaction is selected from aprotic solvents; preferably ether, ketone, nitrile, amide, sulfone, pyridine solvents; more preferably diethyl ether, isopropyl ether, methyl t-butyl ether, butyl ether, ethylene glycol diethyl ether, diethylene glycol dimethyl ether, tetrahydrofuran, 1,4-dioxane, acetone, methyl ethyl ketone, methyl isopropyl ketone, cyclohexanone, methyl hexyl ketone, acetonitrile, propionitrile, dimethylformamide, dimethylacetamide, hexamethylphosphoramide, dimethyl sulfoxide or pyridine; further preferably tetrahydrofuran, 1,4-dioxane, dimethylformamide or acetonitrile.

In some embodiments, in step a), the reaction temperature can be selected from a wide range. In some embodiments, the reaction temperature is selected from −30° C. to 100° C., preferably −20° C. to 80° C., more preferably −15° C. to 70° C., further preferably −10° C. to 60° C.

In some embodiments, in step b), the reaction is carried out in the presence of a base. In some embodiments, the base is selected from a base having a pKa≥12, preferably a base having a pKa≥15, a base having 50≥pKa≥15, a base having 40≥pKa≥15 or a base having 35≥pKa≥15; or the base is preferably NaOH, KOH, LiOH, Mg(OH)$_2$, Ca(OH)$_2$, NaH, KH, sodium methoxide, potassium methoxide, sodium ethoxide, potassium ethoxide, sodium t-butoxide, potassium t-butoxide, KHIVIDS or NaHIVIDS; more preferably NaOH, KOH, LiOH or sodium methoxide. In some embodiments, in step b), the ratio of the compound of formula 10 to the feeding amount of the base (in molar weight) is selected from 1:(5-60), preferably 1:(10-50), more preferably 1:(15-40), further preferably 1:(15-30); or the ratio of the compound of formula 10 to the feeding amount of the base (in molar weight) is preferably 1:5, 1:10, 1:15, 1:20, 1:25, 1:35, 1:40, 1:45, 1:50, 1:55 or 1:60.

In some embodiments, in step b), the reaction is carried out in the presence of a protic solvent selected from $C_{1-6}$ alcohol or water, preferably selected from isopropanol, ethanol, methanol, n-propanol, n-butanol, t-butanol or water; preferably selected from ethanol or water.

In some embodiments, in step b), the reaction temperature is selected from 20° C. to 180° C.; preferably 40° C. to 160° C.; more preferably 60° C. to 140° C.

In some embodiments, in step c), the reaction is carried out in the presence of an acid. In some embodiments, the acid enables the reaction to be carried out under a condition of pH≤6; preferably under a condition of pH≤5.5, pH≤5, pH≤4.5 or pH≤4. In some embodiments, in step c), the acid is selected from protic acids; preferably hydrochloric acid, hydrobromic acid, hydrofluoric acid, sulfuric acid, formic acid, acetic acid, trifluoroacetic acid or p-toluenesulfonic acid; more preferably hydrochloric acid, formic acid, acetic acid, trifluoroacetic acid or p-toluenesulfonic acid.

In some embodiments, in step c), the solvent used in the reaction may be selected from a wide range, for example, may be selected from a protic solvent or/and an aprotic solvent, preferably tetrahydrofuran, dichloromethane, acetonitrile, 1,4-dioxane or dimethylformamide, methanol, ethanol, n-propanol, isopropanol, n-butanol, t-butanol or water.

In some embodiments, in step c), the reaction temperature is selected from −30° C. to 100° C.; preferably −15° C. to 80° C.

In some embodiments, in step d), the alcohol is selected from $C_{1-6}$ alcohol; preferably $C_{1-4}$ alcohol; more preferably methanol, ethanol, propanol or butanol.

In some embodiments, in step d), the reaction is carried out in the presence of an acid. In some embodiments, the acid is selected from a protic acid or a Lewis acid; preferably hydrochloric acid, hydrobromic acid, hydrofluoric acid, sulfuric acid, formic acid, acetic acid, trifluoroacetic acid, p-toluenesulfonic acid, AlCl$_3$, FeCl$_3$ or BF$_3$; more preferably hydrochloric acid, sulfuric acid or p-toluenesulfonic acid.

In some embodiments, in step d), the reaction temperature is selected from 40° C. to 120° C., preferably 60° C. to 100° C.

In some embodiments, in step e), the reaction is carried out in the presence of a base. In some embodiments, the base is selected from triethylamine (TEA), diisopropylethylamine (DIPEA), 1,8-diazabicycloundec-7-ene (DBU), pyridine 2,6-dimethyl pyridine, 4-dimethylaminopyridine (DMAP), imidazole, Na$_2$CO$_3$, K$_2$CO$_3$, Cs$_2$CO$_3$, NaH or KH; preferably TEA, DIPEA, DBU, pyridine, imidazole, Na$_2$CO$_3$ or K$_2$CO$_3$. In some embodiments, in step e), the ratio of the compound of formula 5 to the feeding amount of the base (in molar weight) is selected from 1:(0.5-10), preferably 1:(0.8-8), more preferably 1:(1-6).

In some embodiments, in step e), the solvent used in the reaction is selected from aprotic solvents, preferably diethyl ether, isopropyl ether, methyl t-butyl ether, butyl ether, ethylene glycol diethyl ether, diethylene glycol dimethyl ether, THF, 1,4-dioxane, DCM, ethyl acetate, CH$_3$CN, toluene, xylene, acetone, methyl ethyl ketone, methyl isopropyl ketone, cyclohexanone, methyl hexyl ketone, DMF or DMSO, more preferably THF, DCM, ethyl acetate, CH$_3$CN, toluene, acetone or DMF.

In some embodiments, in step e), the reaction temperature is selected from −10° C. to 100° C., preferably from 0° C. to 60° C.

In some embodiments, in step f), the reaction is carried out in the presence of a reducing agent.

In some embodiments, the reducing agent is selected from lithium aluminum hydride, diisobutylaluminum hydride (DIBAL-H), sodium bis(2-methoxyethoxy)aluminum hydride (Red-Al), BH$_3$, NaBH$_4$, KBH$_4$ or Zn(BH$_4$)$_2$, preferably lithium aluminum hydride.

In some embodiments, in step f), the solvent used in the reaction is selected from a protic or an aprotic solvent, preferably THF, dioxane, methanol, ethanol or t-butyl methyl ether.

In some embodiments, in step f), the reaction temperature is selected from −30° C. to 80° C., preferably −15° C. to 60° C.

In some embodiments, in step g-1), the reaction is carried out in the presence of a base. In some embodiments, the base is selected from a base having a pKa≥5, preferably a base having pKa≥6, pKa≥8, pKa≥10, 30≥pKa≥5, 20≥pKa≥5, 30≥pKa≥6, 30≥pKa≥8, 30≥pKa≥10, 20≥pKa≥6, 20≥pKa≥8, 20≥pKa≥10; in some embodiments, the base is selected from triethylamine (YEA), diisopropylethylamine (DIPEA), 1,8-diazabicycloundec-7-ene (DBU), pyridine, 2,6-dimethyl pyridine, 4-dimethylaminopyridine (DMAP) or imidazole, preferably triethylamine (TEA), diisopropylethylamine (DIPEA), pyridine or imidazole.

In some embodiments, in step g-2), the reaction is carried out under a condition of pH≥7. In some embodiments, preferably, the reaction is carried out under a condition of pH≥7.5, pH≥8 or pH≥8.5. In some embodiments, the base used to regulate the pH may be selected from KHCO$_3$, NaHCO$_3$, K$_2$CO$_3$, or Na$_2$CO$_3$, preferably K$_2$CO$_3$ or Na$_2$CO$_3$. In some embodiments, in step g-2), the feeding amount of the pH-regulating base can be selected from a wide range, as long as it meets carrying out the reaction under suitable pH conditions. In some embodiments, the ratio of the compound of formula 7 to the feeding amount of pH-regulating base (in molar weight) is selected from 1:(0.5-10), preferably 1:(1-8), more preferably 1:(2-6).

In some embodiments, in step g-1), the solvent used in the reaction is selected from an aprotic solvent, preferably diethyl ether, isopropyl ether, methyl t-butyl ether, butyl ether, ethylene glycol diethyl ether, diethylene glycol dimethyl ether, THF, 1,4-dioxane, DCM, ethyl acetate, $CH_3CN$, toluene, xylene, acetone, methyl ethyl ketone, methyl isopropyl ketone, cyclohexanone, methyl hexyl ketone, DMF, DMSO, n-hexane or cyclohexane, more preferably DCM, THF, toluene, n-hexane or cyclohexane.

In some embodiments, in step g-2), the reaction is carried out in the presence of a protic solvent selected from $C_{1-6}$ alcohol or water, preferably selected from isopropanol, ethanol, methanol, n-propanol, n-butanol, tert-butanol or water, more preferably methanol or ethanol.

Intermediate

In another aspect, the application provides the compound of formula 6, the compound of formula 7, the compound of formula 8, the compound of formula 10, and the compound of formula 11,

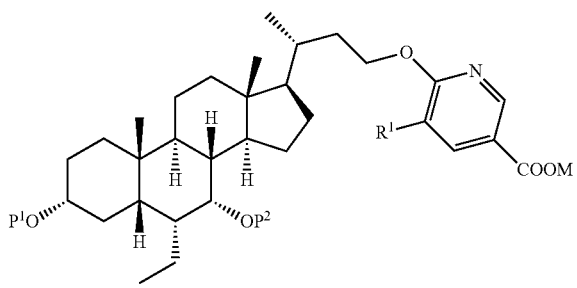

wherein, $R^1$ is selected from H, Cl, Br or F, $R^2$ is selected from methyl, ethyl, propyl or butyl, $P^1$ is selected from a silyl ether protecting group, an alkyl ether protecting group, an alkoxymethyl ether protecting group or an ester protecting group, $P^2$ is selected from a silyl ether protecting group, M is selected from a metal cation.

In another aspect, the application provides use of the compound of formula 6 and the compound of formula 7 in the preparation of the compound of formula 8 or the compound of formula I,

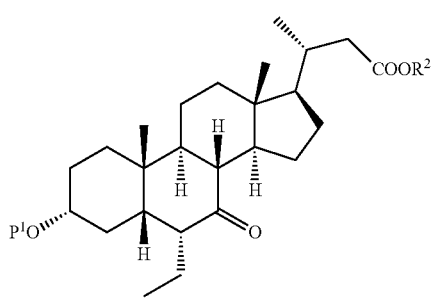

6

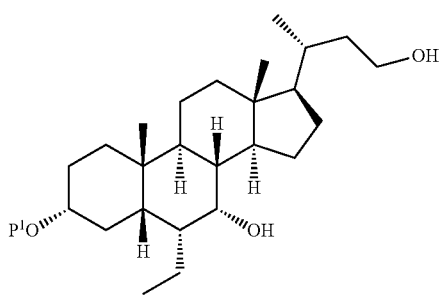

7

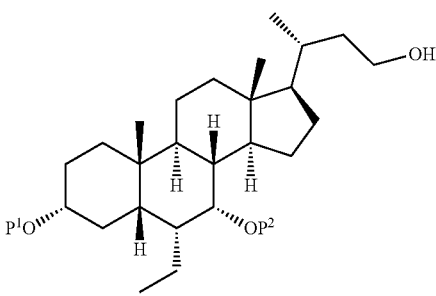

8

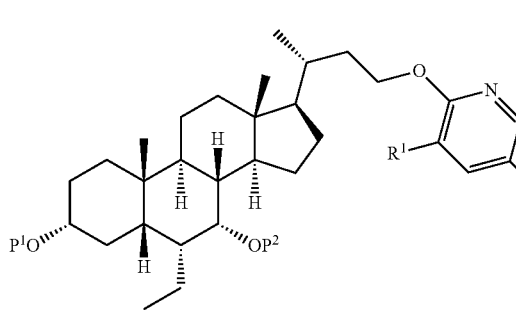

10

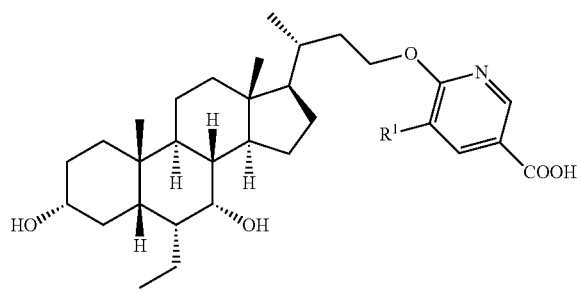

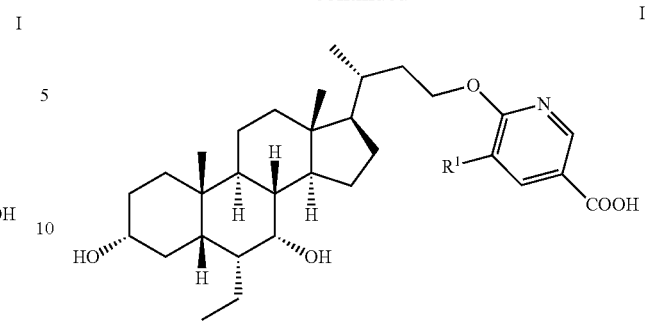

wherein, said R¹ is selected from H, Cl, Br or F, said R² is selected from methyl, ethyl, propyl or butyl, said P¹ is selected from a silyl ether protecting group, an alkyl ether protecting group, an alkoxymethyl ether protecting group or an ester protecting group, said P² is selected from a silyl ether protecting group.

In another aspect, the application provides use of the compound of formula 8, the compound of formula 10, and the compound of formula 11 in the preparation of the compound of formula I,

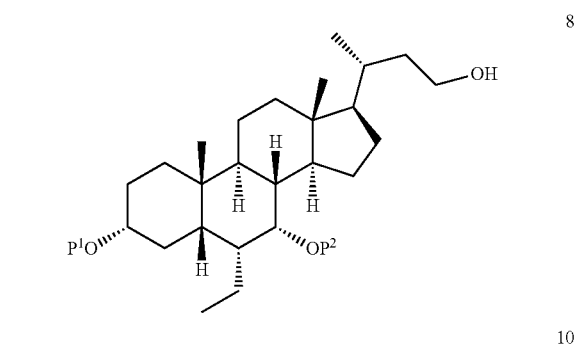

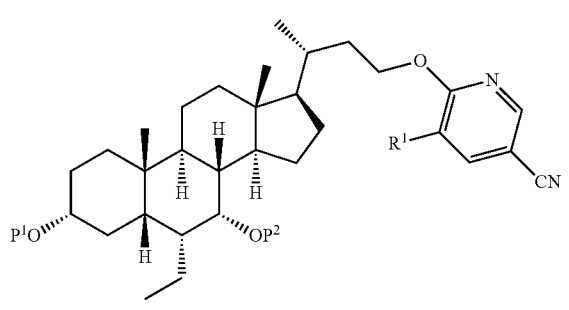

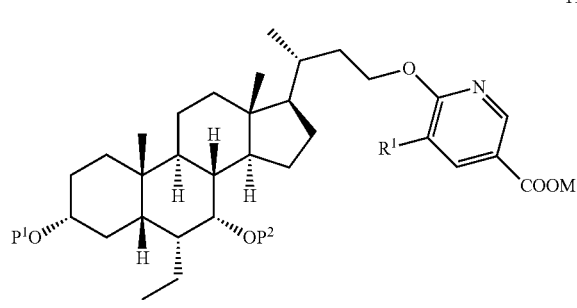

wherein, said R¹ is selected from H, Cl, Br or F, said P¹ is selected from a silyl ether protecting group, an alkyl ether protecting group, an alkoxymethyl ether protecting group or an ester protecting group, said P² is selected from a silyl ether protecting group, said M is selected from a metal cation.

In some embodiments, in the above intermediate or use thereof, said M is selected from an alkali metal cation or an alkaline earth metal cation; preferably $Li^+$, $Na^+$, $K^+$, $Ca^{2+}$ or $Mg^{2+}$; more preferably $Na^+$ or $K^+$.

In some embodiments, in the above intermediate or use thereof, said P¹ is selected from a silyl ether protecting group, an alkyl ether protecting group, an alkoxymethyl ether protecting group or an ester protecting group; preferably trimethylsilyl (TMS), triethylsilyl (TES), t-butyldimethylsilyl (TBDMS), t-butyldiphenylsilyl (TBDPS), benzyl, p-methoxybenzyl, 3,4-dimethoxy benzyl, methyl ether, t-butyl, trityl, 4,4'-dimethoxytrityl (DMTr), methoxymethyl (MOM), benzyloxymethyl (BnOM), tetrahydrofuranyl (THP), formyl, acetyl (Ac), chloroacetyl (CAc), methoxyacetyl (MAc) or pivaloyl (Pv); more preferably trimethylsilyl (TMS), triethylsilyl (TES), t-butyldimethylsilyl (TBDMS), t-butyldiphenylsilyl (TBDPS) or methoxymethyl (MOM).

In some embodiments, in the above intermediate or use thereof, said P² is selected from a silyl ether protecting group; preferably trimethylsilyl (TMS), triethylsilyl (TES), t-butyldimethylsilyl (TBDMS) or t-butyldiphenylsilyl (TBDPS); more preferably trimethylsilyl (TMS).

In some embodiments of the present application, the compound of formula 6 is selected from

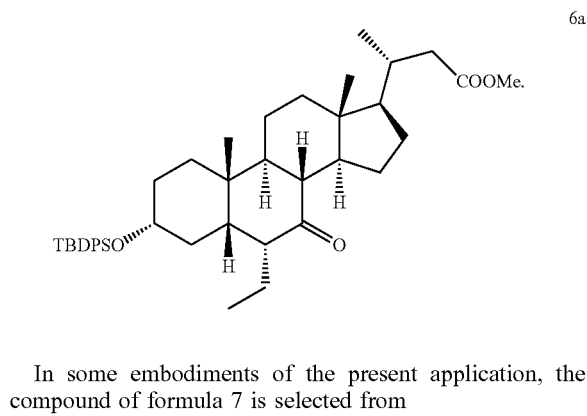

In some embodiments of the present application, the compound of formula 7 is selected from

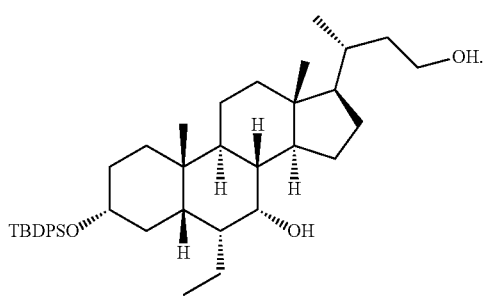

7a

In some embodiments of the present application, the compound of formula 8 is selected from

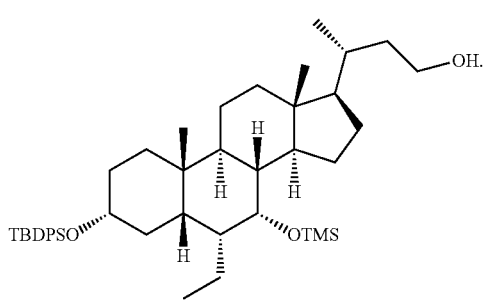

8a

In some embodiments of the present application, the compound of formula 10 is selected from

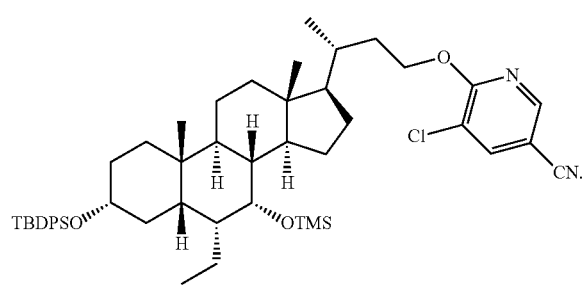

10a

In some embodiments of the present application, the compound of formula 11 is selected from

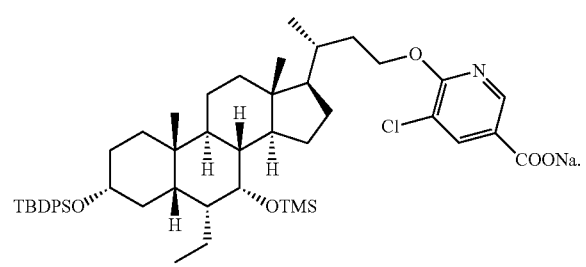

11a

Definitions and Terms

Unless otherwise stated, the terms and phrases used herein have the meanings listed below. A particular term or phrase should not be considered as being indefinite or unclear in the absence of a specific definition, but should be interpreted according to the meaning generally understood by those skilled in the art. When a trade name appears herein, it is intended to refer to corresponding commodity or active ingredient thereof.

In the present application, the alkyl includes all isomeric forms thereof, for example, propyl includes n-propyl, isopropyl; butyl includes 1-n-butyl, 2-n-butyl, isobutyl, t-butyl.

In the present application, the protecting group and the method for attaching or removing the same can be achieved by using a conventional method in the art, and the method can be one-step reaction or multi-step reaction, such as, but not limited to, referring to Greene's Protective Groups in Organic Synthesis—4th Edition published by Wiley Press, or Protecting Groups published by Chemical Industry Press.

In the present application, the compounds may exist in specific geometric or stereoisomeric forms. All such compounds envisaged in the present application include cis and trans isomers, (−)- and (+)-enantiomers, (R)- and (S)-enantiomers, diastereomers, (D)-isomers, (L)-isomers, and racemic mixtures and other mixtures thereof, such as enantiomeric or diastereomeric excess mixtures, and all of these mixtures fall within the scope of the present application. Additional asymmetric carbon atoms may be present in the substituents such as alkyl. All these isomers and mixtures thereof are included in the scope of the present invention.

In the present application, pKa is an acidity coefficient, representing the ability of an acid to dissociate hydrogen ions. According to the common understandings in the art, pKa value of a base is measured by the conjugate acid thereof.

In the present application, the atoms of a steroid compound can be numbered according to the common knowledge in the art, such as, but not limited to, Fundamental Organic Chemistry—Third Edition, edited by Qiyi XING, Higher Education Press. In the present application, taking the compound of formula 7 as an example, the atoms at 3, 7, and 23 positions are labeled as follows:

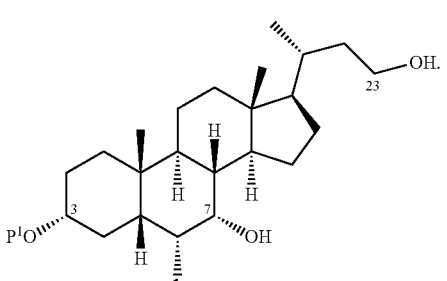

7

Advantageous Effects

The reaction conditions of the preparation method in the present application are mild, and can be carried out, for example, under normal pressure, and the reaction temperature is easy to control. Moreover, some steps in the preparation method described in the present application can simultaneously convert several groups, effectively shortening the steps, and is suitable for industrial production.

DETAILED DESCRIPTION OF THE INVENTION

For better understanding the content of the present invention, the following detailed description is made in combination with the specific examples, but the specific examples are not intended to limit the content of the present invention.

Preparation Example 1: Preparation of the Compound of Formula 8a

Step 1-1 Preparation of a Compound of Formula 5a

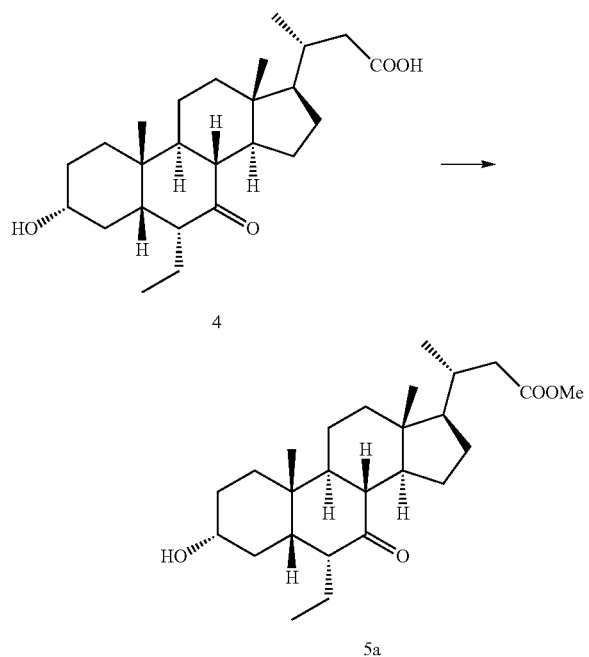

Methanol (33 L) was added into a 50 L reactor at 25° C. Substrate 4 (3.330 kg, 8.23 mol) was added into the reactor, followed by adding p-toluenesulfonic acid monohydrate (156.6 g, 0.823 mol) thereto. The reaction was heated to 60° C. and stirred at this temperature for 12 hours. The reaction was monitored by TLC, which showed disappearance of starting materials. HPLC showed that about 100% product was generated. The reaction solution was cooled to room temperature, and then the pH value thereof was regulated to about 9 with a saturated sodium bicarbonate solution. The solution was dried by rotary evaporation to give a crude product. The crude product was dissolved in ethyl acetate (30 L), and then washed by saturated sodium bicarbonate solution (9 L), water (9 L) and saturated brine (9 L) successively. The organic phase was dried by rotary evaporation to give the product, which was a brown oily liquid.

$^1$H NMR (400 MHz, CDCl$_3$) δ 3.66 (s, 3H), 3.61-3.49 (m, 1H), 2.74-2.66 (m, 1H), 2.48-2.33 (m, 2H), 2.24-2.15 (m, 1H), 2.07-1.61 (m, 13H), 1.54-1.40 (m, 3H), 1.31-1.07 (m, 6H), 1.02-0.77 (m, 9H), 0.69 (s, 3H).

Step 1-2 Preparation of the Compound of Formula 6a

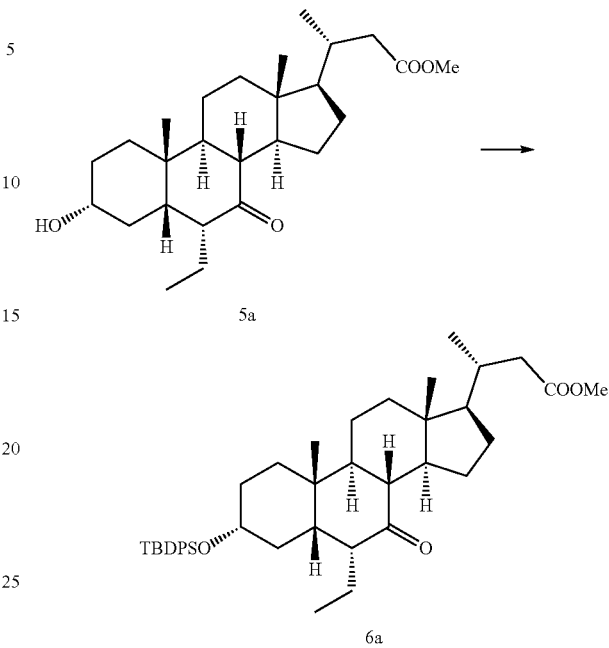

The compound of formula 5a (3100 g) was dissolved in dichloromethane (30 L), and then imidazole (529.4 g) and triethylamine (786.8 g) were sequentially added thereto. The temperature of the reactor was lowered (internal temperature thereof was 5° C.). At this temperature, TBDPSCl (2140 g) was slowly added dropwise, and during which the temperature did not exceed 10° C. After the dropwise addition was completed, the reaction was stirred at room temperature for 16 hours. TLC showed that the starting material was completely reacted, and 15 L of water was slowly added dropwise to the reaction mixture to quench the reaction. After standing, the reaction product was separated, and the lower dichloromethane phase was separated out. The dichloromethane phase was washed with saturated brine (10 L), and the organic phase was concentrated to give a product, which was a brown oily liquid.

$^1$H NMR (400 MHz, CDCl$_3$) δ 7.69-7.63 (m, 4H), 7.45-7.34 (m, 6H), 3.77 (br t, J=6.1 Hz, 1H), 3.69 (s, 3H), 3.54-3.44 (m, 1H), 2.57 (q, J=6.1 Hz, 1H), 2.46 (br dd, J=3.0, 14.6 Hz, 1H), 2.36-2.21 (m, 2H), 2.08-1.67 (m, 9H), 1.62-1.17 (m, 12H), 1.12-0.87 (m, 14H), 0.70-0.62 (m, 6H).

Step 1-3 Preparation of the Compound of Formula 7a

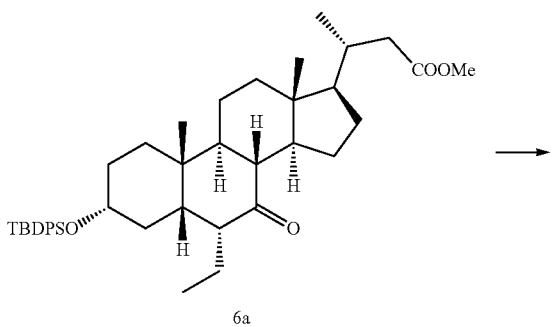

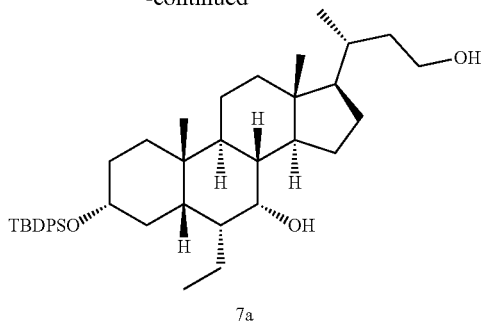

7a

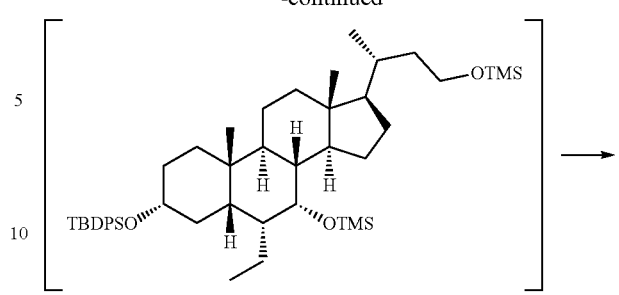

Tetrahydrofuran (10 L) was added to a 50 L reactor at 15° C., and LiAlH₄ (235 g, 6.2 mol) was added to the reactor under N₂ protection. The reactor was cooled down to an internal temperature of 5° C. After dissolving the compound of formula 6a (2.04 kg) in tetrahydrofuran, it was slowly added dropwise to a solution of LiAlH₄ in tetrahydrofuran over approximate 2.5 hours. The reaction was stirred at 15° C. for 2 hours, and monitored by TLC to show that starting materials were disappeared. H₂O (235 mL) was slowly added dropwise to the reaction solution to quench the reaction, then tetrahydrofuran solution (20 L) was added to the reaction solution, and 15% NaOH solution (235 mL) was slowly added dropwise to the reaction solution, stirred for 12 hours. The reaction solution was filtered, and the filter cake was washed with dichloromethane (3 L). The filtrate was dried by rotary evaporation to give an oil. After dissolving the oil in DCM (15 L), the organic phase was washed once with water (5 L) and once with saturated brine (5 L), and the filtrate was dried by rotary evaporation to give a white solid (1.8 kg). The reaction solution was cooled down to room temperature (about 16° C.), then pH thereof was regulated to about 9 with saturated sodium bicarbonate solution, and the solution was dried by rotary evaporation (only small amount remaining) to obtain a crude product, which was dissolved in ethyl acetate (30 L), washed by saturated sodium bicarbonate solution (9 L), water (9 L), and saturated saline (9 L) successively. The organic phase was dried by rotary evaporation to give a product, which was a brown oily liquid.

¹H NMR (400 MHz, CDCl₃) δ 7.64-7.58 (m, 4H), 7.37-7.25 (m, 6H), 3.68-3.52 (m, 3H), 3.38-3.28 (m, 1H), 1.91-1.03 (m, 25H), 1.02-0.93 (m, 11H), 0.88 (d, J=6.5 Hz, 3H), 0.72-0.64 (m, 6H), 0.57 (s, 3H).

Step 1-4 Preparation of the Compound of Formula 8a

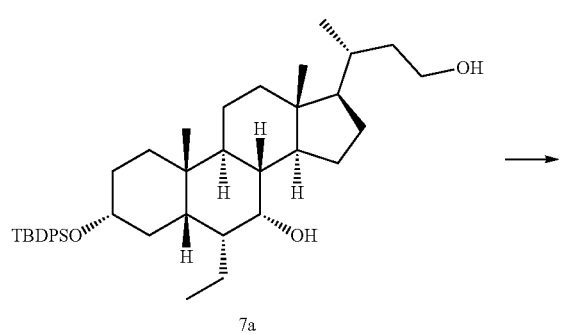

7a

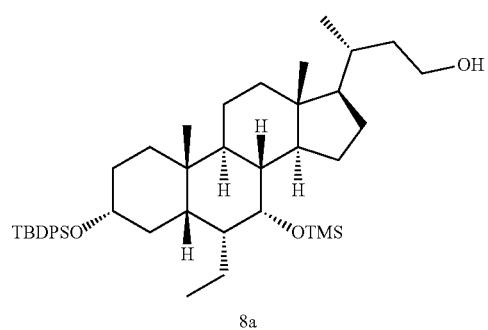

8a

Imidazole (1.14 kg, 16.73 mol) was added into a solution of the compound of formula 7a (3.52 kg, 5.58 mol) in anhydrous dicholomethane (35 L). Trimethylchlorosilane (1770 mL, 13.95 mol) was added dropwise into the system at 5° C. over two hours. The system was stirred at 15° C. for 3 hours. TLC detection showed that the reaction was almost completed. 10 liters of water was added to the system at 15° C., which was stirred and separated. The organic phase was washed once with 10 liters of water and 10 liters of saturated brine successively.

The organic phase was concentrated to about 5 liters, and 30 liters of ethanol was added to the solution. Potassium carbonate (1.93 kg, 13.95 mol) was added to the solution at 15° C. The system was stirred at 15° C. for 14 hours. TLC detection showed that the reaction was almost completed. The reaction solution was filtered. The filter cake was rinsed with 3 liters of dichloromethane. The filtrate was concentrated to give an oil. The oil was dissolved in 20 liters of dichloromethane and washed once with 10 liters of water and 10 liters of saturated brine successively. The organic phase was dried over 3 kg of anhydrous sodium sulfate and filtered, purified by silica gel column chromatography (100-200 mesh, 230 mm×800 mm), and eluted with n-heptane: ethyl acetate=30:1-20:1. The title compound 8a (3.20 kg, 82% yield, 87% purity) was obtained.

¹H NMR (400 MHz, CDCl₃): δ 7.77-7.64 (m, 4H), 7.45-7.32 (m, 6H), 3.78-3.56 (m, 3H), 3.43-3.31 (m, 1H), 1.98-1.13 (m, 24H), 1.07 (s, 9H), 0.97 (d, J=6.5 Hz, 3H), 0.83-0.74 (m, 4H), 0.68-0.55 (m, 6H), 0.17-0.05 (m, 9H).

Preparation Example 2: Preparation of a Compound of Formula I-Cl

Step 2-1 Preparation of the Compound of Formula 10a

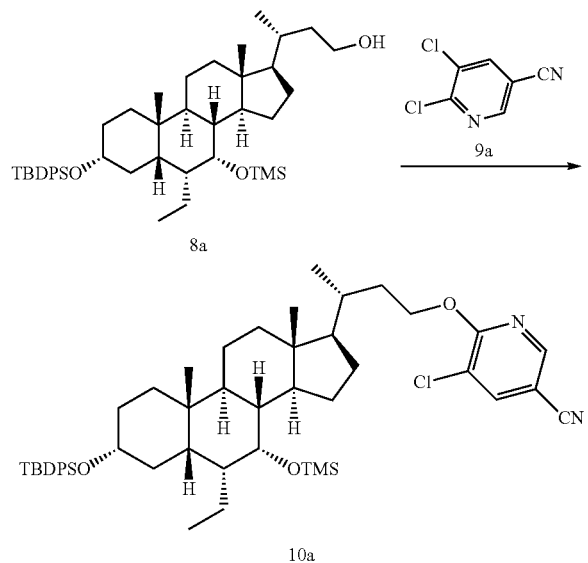

Step 2-2 Preparation of the Compound of Formula 11a

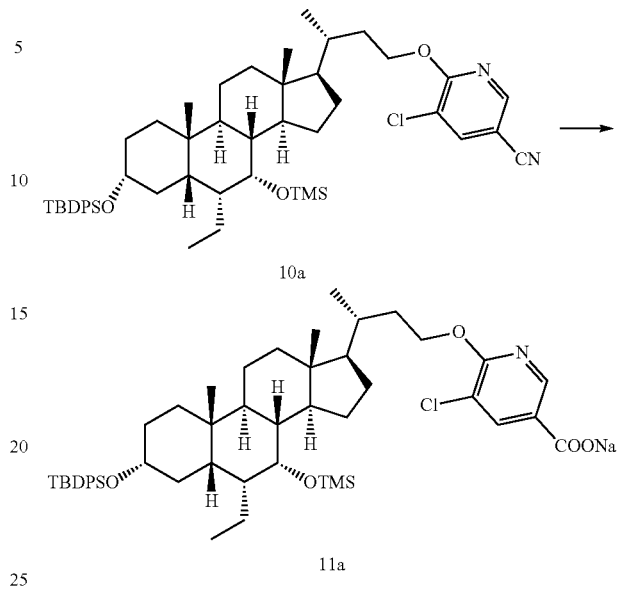

The compound of formula 8a (2498.0 g, 3.10 mol) was added into the reactor and dissolved in THF (12.5 L), and the internal temperature was controlled from 5° C. to 10° C. t-BuONa (614.2 g, 6.20 mol) was slowly added thereto over about 40 min. After being stirred for 10 min, it was heated up to 20° C. to 23° C., with stirring for 1.5 h, and then cooled down to 5° C. to 10° C. While maintaining the internal temperature, a THF solution of a compound of formula 9a (12.5 L, 6.20 mol, 1073.1 g) was added dropwise to the reaction solution, which was heated up to 60° C. After stirring for 1.5 h, TLC and HPLC detections showed that the reaction was completed, and the temperature was lowered to 20° C. It was quenched by adding 25 L of water and extracted with ethyl acetate (25 L×2). The organic phases were combined and washed three times with saturated brine (25 L×3), and then dried by rotary evaporation to give an oily crude product. The crude product was dissolved in 2.5 L of acetone. A total of 6.6×3 L of methanol was added into three 10 L three-neck flasks. The solution of the crude product was slowly added dropwise while controlling the internal temperature from −10° C. to −15° C., stirred, and a large amount of solid was precipitated. After filtration, the filter cake was washed with 3.0 L of methanol to obtain a yellow solid (undried), and the yellow solid was added to 18.0 L of methanol, slurried overnight. After filtration, the filter cake was washed with 3.0 L of methanol to obtain a yellow solid (undried), and the yellow solid was added to 18.0 L of methanol, slurried overnight. After filtration, the filter cake was washed with 2.0 L of methanol, dried under vacuum for 24 h, to give 2522.0 g of a yellow solid, i.e., the compound of formula 10a (2522.0 g, 90% yield, 92.9% purity).

$^1$H NMR (400 MHz, CHLOROFORM-d) δ=8.25 (d, J=2.0 Hz, 1H), 7.73 (d, J=2.0 Hz, 1H), 7.63-7.51 (m, 4H), 7.33-7.21 (m, 6H), 4.48-4.27 (m, 2H), 3.50 (s, 1H), 3.31-3.18 (m, 1H), 1.98-1.03 (m, 27H), 0.95 (s, 9H), 0.73-0.64 (m, 4H), 0.58-0.46 (m, 6H), 0.00 (s, 9H).

The compound of formula 10a (2520.0 g, 2.79 mol) was added into a reactor (20 L), then EtOH (13.0 L) was added thereto, stirred to dissolve, and the internal temperature thereof was controlled to about 10° C. An aqueous solution (13.0 L) of NaOH (2232.0 g, 55.8 mol) was added thereto in portions. After the temperature was heated up to 105° C., it was stirred for 2.8 hours. TLC and HPLC detections shown that the reaction was completed. The reaction solution was cooled down to 10° C., and let it stand still for two hours. Solids were precipitated on the bottom of the reactor. 19.5 L of the supernatant was drawn out, 39.0 L of water was added into the reaction solution. The internal temperature was controlled at 12° C., and it was stirred for 36 h. After filtration, the solid was washed with 6.0 L of water and 6.0 L of acetonitrile successively. The solid was slurried with 10.0 L of acetonitrile for 2 hours, and it was filtered to give a solid. It was slurried with 12.0 L of acetone for 16 hours. After filtration, a solid was obtained, which was slurried again with 12.0 L of acetone for 16 hours. After filtration, the product was dried to give 2332.3 g of a white solid, i.e., the compound of formula 11a (2332.3 g, 94.7% yield, 99.7% purity).

$^1$H NMR (400 MHz, METHANOL-d$_4$) δ=8.48 (d, J=2.0 Hz, 1H), 8.07 (d, J=2.0 Hz, 1H), 7.55 (br dd, J=6.5, 12.5 Hz, 4H), 7.41-7.11 (m, 6H), 4.52-4.15 (m, 2H), 3.54 (br s, 1H), 3.34-3.22 (m, 1H), 2.04-1.14 (m, 28H), 0.93 (s, 9H), 0.69 (s, 4H), 0.60-0.43 (m, 6H), 0.00 (s, 9H).

Step 2-3 Preparation of the Compound of Formula I-Cl

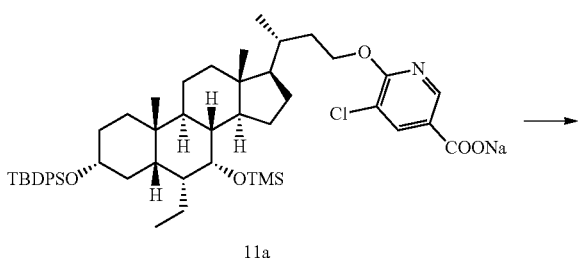

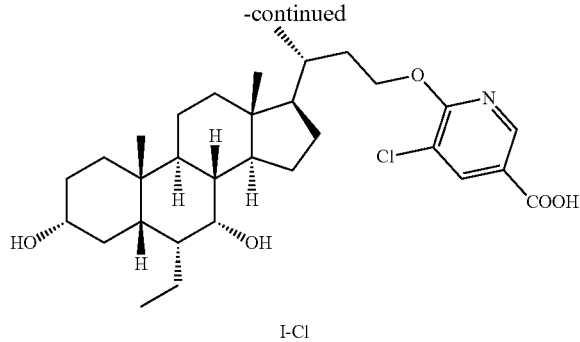

I-Cl

The compound of formula 11a (2330.3 g, 2.65 mmol) was added into a reactor (50 L), and THF (24.0 L) was added thereto for dissolving. The internal temperature was controlled at 10° C., and a concentrated HCl (10.0 L, 120.00 mol) liquid was slowly added dropwise thereto, which was heated up to 13° C. (room temperature) over 2 hours and then stirred for 90 hours. Along with TLC detection, 75 L of sodium hydroxide solution (6000 g) was slowly added dropwise at 8° C. to 10° C. to regulate the pH to 10, and then it was stirred for half an hour, and extracted with methyl t-butyl ether (30 L×4). After the pH was regulated to 5 with concentrated HCl (3000 mL), it was extracted with ethyl acetate (30 L×2). The organic phase was washed with water (30 L×4), and concentrated to give 1350 g of solid. The solid was slurried with a mixed solvent of 2.0 L of ethyl acetate and 5.0 L of n-heptane overnight and filtered to give 1280 g of solid. After being dissolved to clear with 9.0 L of ethyl acetate (80° C.), it was slowly cooled down to room temperature (10° C.), filtered to give 1222 g of the title compound.

$^1$H NMR (400 MHz, METHANOL-$d_4$) δ=8.69 (d, J=2.0 Hz, 1H), 8.23 (d, J=2.0 Hz, 1H), 4.67-4.30 (m, 2H), 3.67 (br s, 1H), 3.34-3.22 (m, 1H), 2.10-1.11 (m, 25H), 1.09-0.97 (m, 3H), 0.96-0.86 (m, 6H), 0.73 (s, 3H).

Pharmacological or pharmacokinetic evaluations were performed for the following compounds:

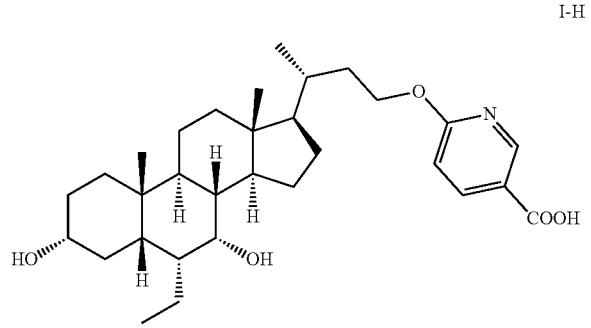

I-H

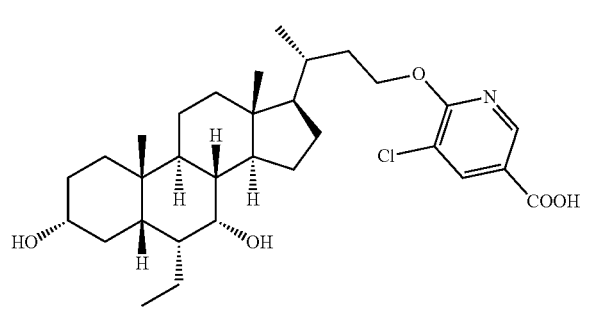

I-Cl

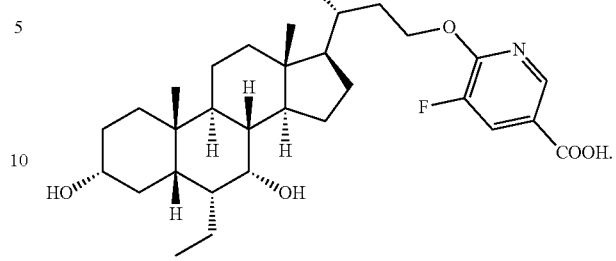

I-F

Experimental Example 1: In Vitro Evaluation

FXR Biochemical Experiment

Experiment Purpose

The activation of compounds on FXR binding reaction was examined by a homogeneous proximity luminescenceamplification test (alphascreen).

Experiment Materials

1. Protein: glutathione-S-transferase-labeled FXR human protein (Invitrogen)

2. Co-activator: Biotin-labeled steroid receptor coactivator (Anaspec)

3. Detection reagent: homogeneous proximity luminescence amplification test (alphascreen) Detection Kit (PerkinElmer)

Experiment Method

1. Compound dilution: the test compound was prepared as a 40 μM DMSO solution, and then diluted 3-fold to 10 concentration points. The reference compound was prepared as a 400 μM DMSO solution, followed by diluted 1.5-fold to 10 concentration points. The diluted DMSO solution was added to the wells of a 384-well plate in a volume of 150 nL per well.

2. Glutathione-S-transferase-labeled FXR human protein and biotin-labeled steroid receptor coactivator were formulated as mixed solutions with concentrations of 0.4 nM and 30 nM, respectively, which was added to the wells of the 384-well plate in a volume of 15 per well, and the plate was incubated for 1 hour at room temperature.

4. The mixed solution of acceptor beads in the homogeneous proximity luminescence amplification test (alphascreen) Detection Kit was diluted 125-fold and added to the wells of the 384-well plate in a volume of 7.5 μL per well. The experiment process was carried out with protecting from light. The incubation was performed for 1 hour at room temperature.

5. The mixed solution of donor beads in the homogeneous proximity luminescence amplification test (alphascreen) Detection Kit was diluted 125-fold and added to the wells of the 384-well plate in a volume of 7.5 μL per well. The experiment process was carried out by protecting from light. The incubation was performed for 1 hour at room temperature.

6. $EC_{50}$ test: the absorbance signals at 520-620 nm were read by using Envision under the excitation at the wavelength of 680 nm.

7. Analytical data: the data were analyzed by using Prism 5.0 to calculate the $EC_{50}$ value of the activation of the compound. Then, the ratio of the highest signal value of the compound to the highest signal value of the reference compound was calculated to give the percentage of activation efficacy of the compound (Efficacy).

FXR Cell Experiment

Experiment Purpose

The effect of the compound on the cellular functional activity was examined by the β-lactamase reporter gene technique.

Experiment Materials

1. Cell line: FXR HEK 293T DA
2. Cell culture medium: DMEM medium supplemented with 10% serum and Penicillin/Streptomycin (1×).
3. Detection reagent: GeneBLAzer® Reporter Gene Detection Kit (Invitrogen)

Experiment Method

1. Compound dilution: the test compound was prepared as a 100 μM DMSO solution, and then the compound was diluted 3-fold to 10 concentration points. The reference compound was prepared as a 100 μM DMSO solution, and then diluted 1.3-fold to 10 concentration points. The diluted DMSO solution was added to the wells of a 384-well plate in a volume of 200 nL per well.
2. Cell inoculation: FXR HEK 293T DA cells were resuscitated, resuspended in culture medium, diluted to a density of $5\times10^5$/mL, and added to the wells of a 384-well plate in a volume of 40 μL per well.
3. The 384-well microplate was incubated at 37° C., 5% $CO_2$ for 16 hours.
4. 6 μL of 1 mM LiveBLAzer™-FRET B/G (CCF4-AM) substrate was mixed with 60 μL of B solution and 934 μL of C solution, which was added to the wells of a 384-well plate in a volume of 8 μL per well.
5. The 384-well microplate was incubated in dark for 2 hours at room temperature.
6. $EC_{50}$ test: the absorbance signals at 460 nm and 530 nm were read by using Envision under the excitation at the wavelength of 409 nm.
7. Analytical data: the data were analyzed by using Prism 5.0 to calculate the $EC_{50}$ value of the activation of the compound. Then, the ratio of the highest signal value of the test compound to the highest signal value of the reference compound (chenodeoxycholic acid, CDCA) was calculated to give the percentage of activation efficacy of the compound (Efficacy).

TABLE 1

Test results of $EC_{50}$ for the biochemical experiment and cell experiment

| Test sample | FXR enzymatic activity | | FXR cell viability | |
|---|---|---|---|---|
| | $EC_{50}$ (μM) | Efficacy | $EC_{50}$ (μM) | Efficacy |
| Chenodeoxycholic acid, CDCA | 12.14 | 100% | 10.22 | 100% |
| The compound of formula I-H | 0.006 | 249% | | |
| The compound of formula I-Cl | 0.0025 | 248% | 0.003 | 150% |
| The compound of formula I-F | 0.0025 | 138% | | |

Conclusion: the agonistic effect of the compound of the present application on the FXR receptor was significant, and the agonistic effect on the FXR receptor was also significant at the cellular level.

Experimental Example 2: In Vivo Study

Pharmacokinetics in Mice Administrated with Single Compound

Twelve C57BL/6J male mice were randomly divided into two groups, 6 mice in each group. The first group was the intravenous group, who was administered in 2 mg/kg and 2 mL/kg through the tail vein injection (the solvent was 10% HPbCD aqueous solution, and if the drug solubility was not ideal, a co-solvent would be added); the second group was the oral group, who was intragastrically administered in 10 mg/kg, 10 mL/kg (the solvent was 0.5% HPMC aqueous solution). Plasma (using $K_2$-EDTA as anticoagulant) samples were taken at 0.083, 0.25, 0.5, 1, 2, 4, 6, 8 and 24 hours after administration for the intravenous group; and plasma samples were taken at 0.25, 0.5, 1, 2, 4, 6, 8 and 24 hours after administration for the oral group. For 6 animals in each group, blood samples were collected for 3 animals at one time point, and the first batch of 3 animals was alternately sampled with the second batch of 3 animals. Plasma sample analysis was performed by using LC-MS/MS. The obtained plasma concentrations were plotted against time, and PK parameters were calculated by using Phoenix WinNonlin 6.3.

TABLE 2

| | Compound | Obeticholic acid | The compound of formula I-H | The compound of formula I-Cl |
|---|---|---|---|---|
| | Dosage (mg/kg) | 10 | 10 | 10 |
| PK parameter in plasma | $c_{max}$ (nM) | 1013 | 936 | 1777 |
| | $T_{max}$ (h) | 0.3 | 0.5 | 0.5 |
| | AUC (nM · h) | 993 | 2337 | 1109 |
| | F % | 13% | 34% | 20% |

Conclusion: as shown in Table 2, after oral administration at the same dosage, the peak concentration of the compound of formula I-H was close to that of the control compound obeticholic acid, and the drug exposure was higher than that of the control compound obeticholic acid. After oral administration at the same dosage, the peak concentration of the compound of formula I-Cl was higher than that of the control compound obeticholic acid, and the drug exposure was also higher than that of the control compound obeticholic acid.

Liver-Blood Ratio Experiment of Mice Via Cassette Dosing

Six C57BL/6J male mice were grouped as one oral group. The preparation contained 5 kinds of the developed drugs, and 2 mg/kg/compound was intragastrically administered (the solvent was 0.5% HPMC aqueous solution). The five compounds were firstly dissolved in the solvent, respectively, by ultrasonication or vortex, to form 1 mg/mL solutions (clear solution or suspension), and then the solutions of the five compound were mixed in equal volumes (1:1:1:1:1, v:v:v:v:v) in a glass bottle. After intragastrical oral administration, plasma and liver tissue samples were collected from 3 animals at 0.5 hours after administration; corresponding samples were collected from the other 3 animals at 3 hours after administration. After collection, the liver tissue was homogenized by using ice-cold homogenization buffer (methanol: 15 mM PBS buffer (pH 7.4)=1:2, v:v) according to liver weight: homogenization buffer volume=1:3. Plasma and liver tissue samples were analyzed by using a five-in-one LC-MS/MS analysis method developed in advance. Plasma concentrations and liver tissue homogenate concentrations were obtained, and the concentration ratio of liver tissue to plasma was calculated by using Excel.

TABLE 3

|  | Compound | Obeticholic acid | The compound of formula I-H |
|---|---|---|---|
| PK parameters | Dosage (mg/kg) | 2 | 2 |
| | Liver concentration (nM) 0.5 h/3 h | 711/625 | 1959/701 |
| | Plasma concentration (nM) 0.5 h/3 h | 151/63 | 83/45 |
| | Liver/plasma concentration ratio 0.5 h/3 h | 5/10 | 24/16 |

Conclusion: as shown in Table 3, after oral administration of the compound of the present application at the same dosage, the drug concentrations of the compound of formula I-H in the liver were higher than those of the control compound at 0.5 hours and 3 hours, and the liver/plasma concentration ratios were also higher than those of the control compound at 0.5 hours and 3 hours.

What is claimed is:

1. A preparation method for a compound of formula I,

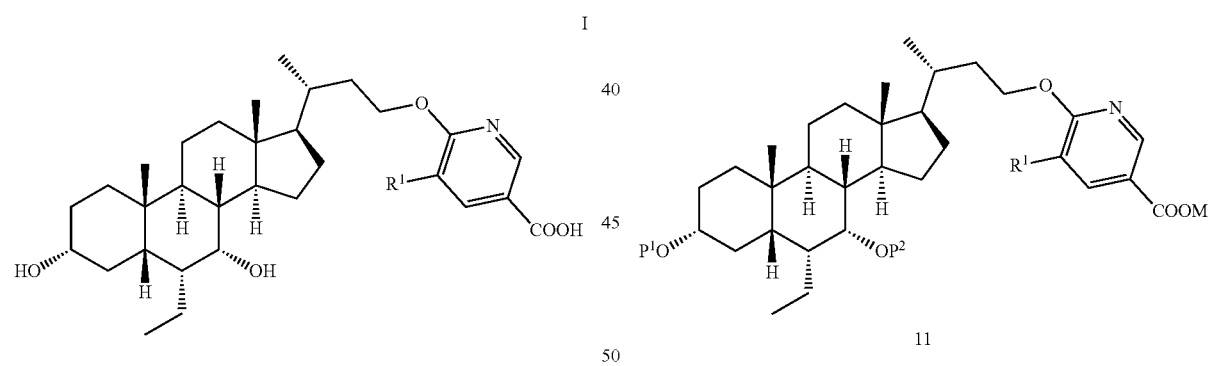

comprising:

a), reacting a compound of formula 8 with a compound of formula 9 to obtain a compound of formula 10,

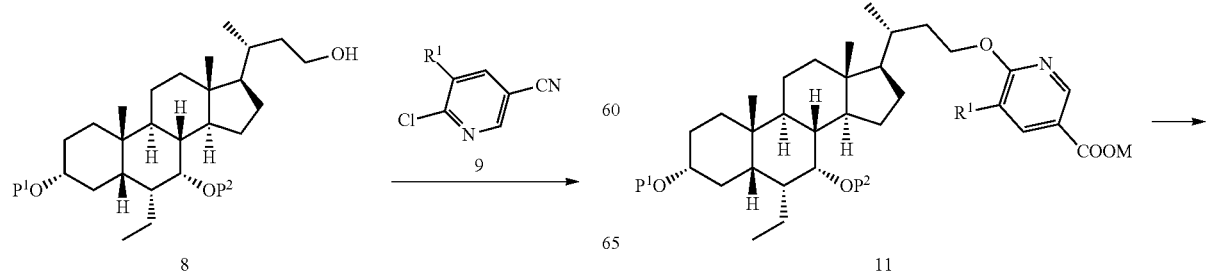

b), reacting from the compound of formula 10 to obtain a compound of formula 11, and c), reacting from the compound of formula 11 to obtain the compound of formula I,

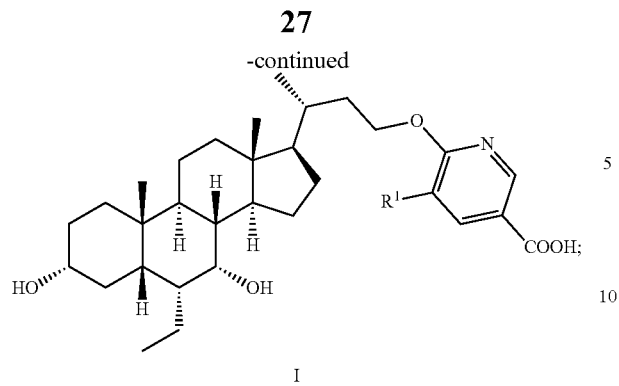

I wherein, R¹ is selected from H, Cl, Br or F,

P¹ and P² are each independently selected from a hydroxy protecting group, and

M is selected from a metal cation.

2. The preparation method according to claim 1, wherein said P¹ and P² are each independently selected from a hydroxy protecting group that keeps attaching to an oxygen atom at position 3 or/and at position 7 on the steroid compound under basic conditions.

3. The preparation method according to claim 1, wherein said P¹ is selected from a silyl ether protecting group, an alkyl ether protecting group, an alkoxymethyl ether protecting group, or an ester protecting group.

4. The preparation method according to claim 1, wherein said P² is selected from a silyl ether protecting group.

5. The preparation method according to claim 1, wherein said M is selected from an alkali metal cation or an alkaline earth metal cation.

6. The preparation method according to claim 1, wherein in a), the reaction is carried out in the presence of a base.

7. The preparation method according to claim 1, wherein in b), the reaction is carried out in the presence of a base.

8. The preparation method according to claim 1, wherein in c), the reaction is carried out in the presence of an acid.

9. The preparation method according to claim 1, further comprising:

d), subjecting a compound of formula 4 used as a starting material to an esterification reaction with an alcohol to obtain a compound of formula 5,

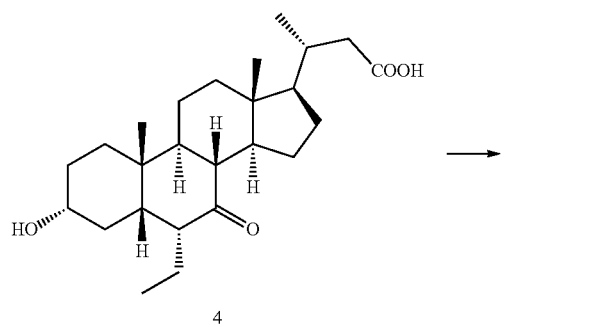

4

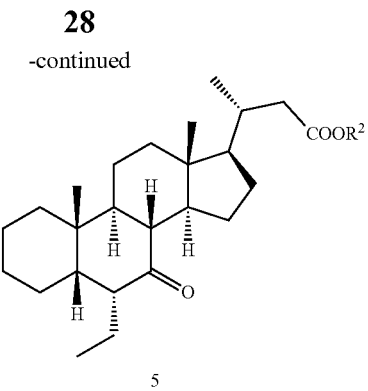

5 e), attaching a protecting group to 3-hydroxyl on the compound of formula 5 to obtain a compound of formula 6,

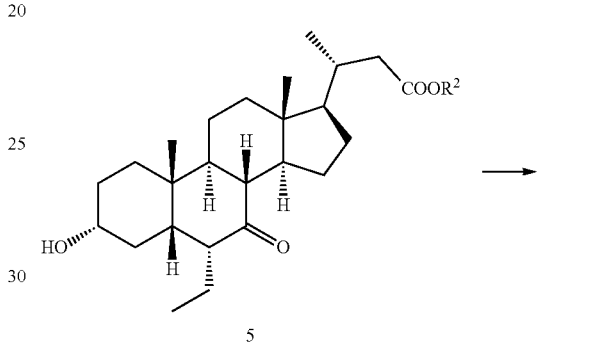

5

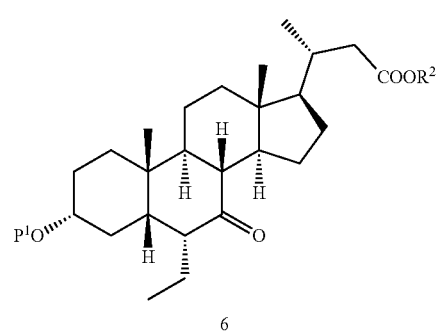

6 f), reacting from the compound of formula 6 to obtain a compound of formula 7,

6

-continued

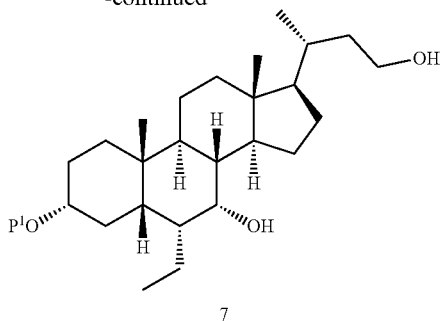

7 g-1), attaching a protecting group P² to 7-hydroxyl and 23-hydroxyl on the compound of formula 7 to obtain a compound of formula 12, step g-2), and removing 23-hydroxy protecting group P² from the compound of formula 12 to obtain the compound of formula 8,

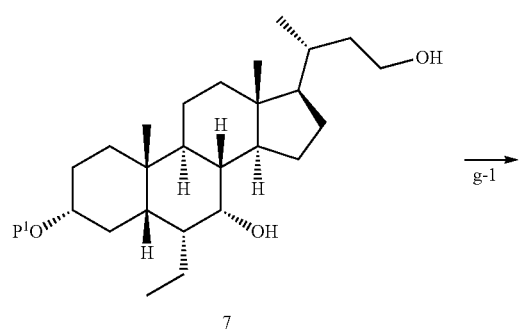

7

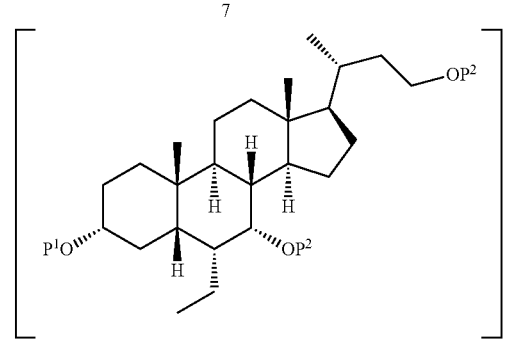

12

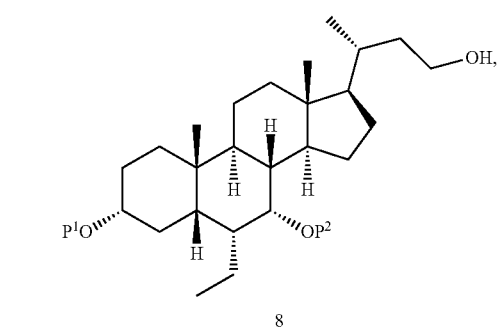

8 wherein, R² is selected from C₁₋₆ alkyl.

10. The preparation method according to claim 9, wherein said R² is selected from C₁₋₄ alkyl.

11. A preparation method for a compound of formula 8, comprising:

a), subjecting a compound of formula 4 used as a starting material to an esterification reaction with an alcohol to obtain a compound of formula 5,

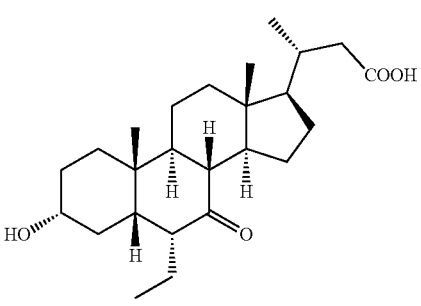

4

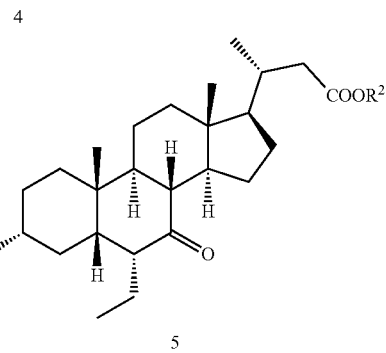

5 b), attaching a protecting group to 3-hydroxyl on the compound of formula 5 to obtain a compound of formula 6,

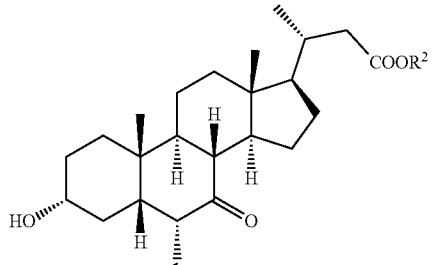

5

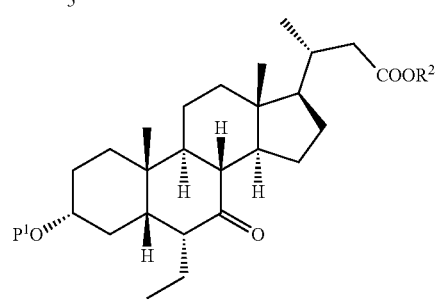

6 c), reacting the compound of formula 6 to obtain a compound of formula 7,

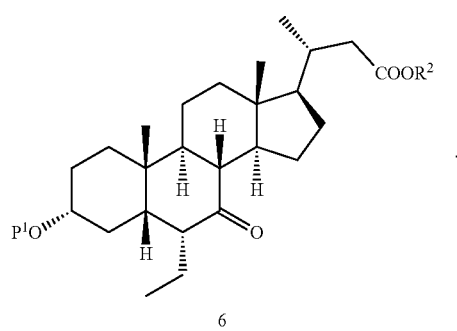

6

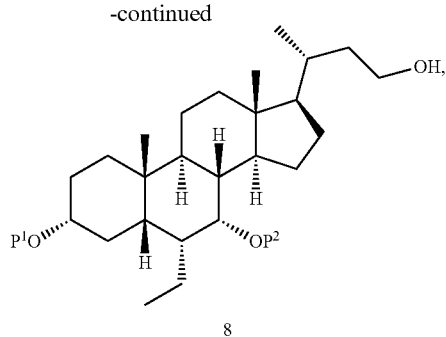

8

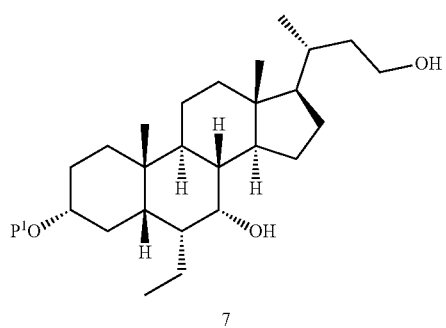

7 d), attaching a protecting group P² to 7-hydroxyl and 23-hydroxyl on the compound of formula 7 to obtain a compound of formula 12, and e), removing 23-hydroxy protecting group P² from the compound of formula 12 to obtain the compound of formula 8,

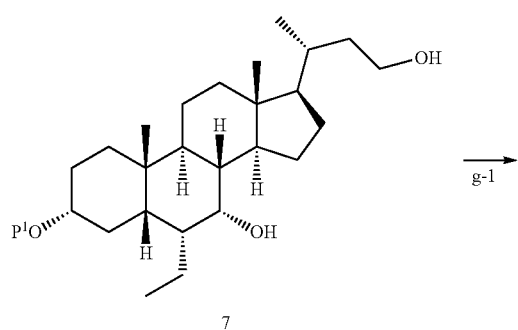

7

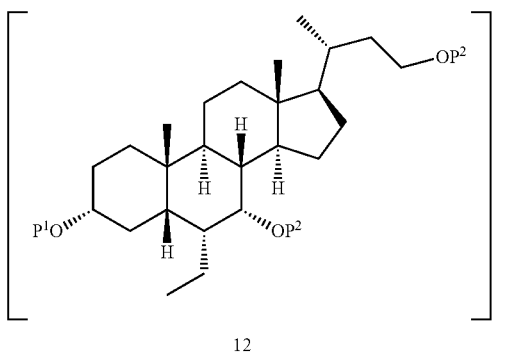

12 wherein, P¹ and P² are each independently selected from a hydroxy protecting group, and R² is selected from $C_{1-6}$ alkyl.

12. The preparation method according to claim 11, wherein said P¹ and P² are each independently selected from a protecting group being able to effectively protect 3-hydroxyl or/and 7-hydroxyl on the steroid compound under non-acidic condition.

13. The preparation method according to claim 11, wherein said P¹ is selected from a silyl ether protecting group, an alkyl ether protecting group, an alkoxymethyl ether protecting group, or an ester protecting group.

14. The preparation method according to claim 11, wherein said P² is selected from a silyl ether protecting group.

15. The preparation method according to claim 11, wherein said R² is selected from $C_{1-4}$ alkyl.

16. A compound represented by following formulae:

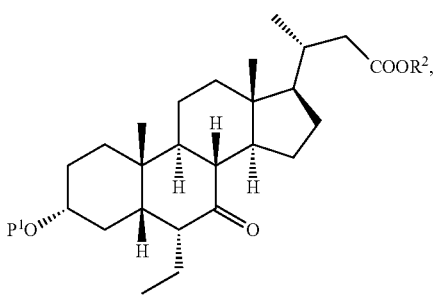

6 wherein R² is selected from methyl, ethyl, propyl or butyl, and P¹ is selected from a silyl ether protecting group, an alkyl ether protecting group, an alkoxymethyl ether protecting group or formyl, chloroacetyl, methoxyacetyl or pivaloyl;

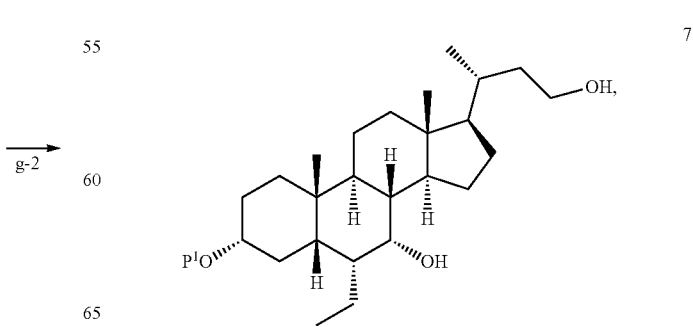

7 wherein P¹ is selected from trimethylsilyl, triethylsilyl, t-butyldiphenylsilyl, an alkyl ether protecting group, an alkoxymethyl ether protecting group or formyl, chloroacetyl, methoxyacetyl or pivaloyl;

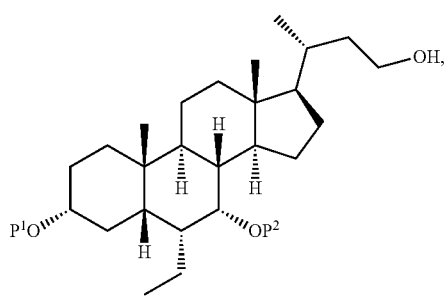

wherein P¹ is selected from trimethylsilyl, triethylsilyl, t-butyldiphenylsilyl, an alkyl ether protecting group, an alkoxymethyl ether protecting group or an ester protecting group, and P² is selected from a silyl ether protecting group;

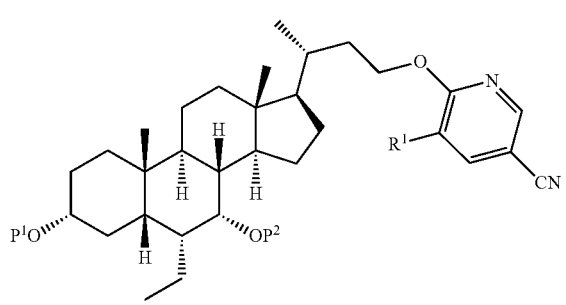

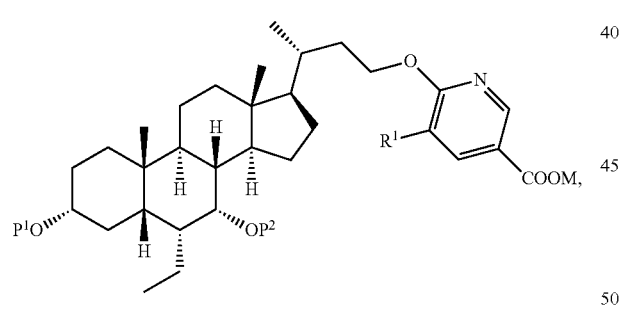

wherein, R¹ is selected from H, Cl, Br or F,
P¹ is selected from a silyl ether protecting group, an alkyl ether protecting group, an alkoxymethyl ether protecting group or an ester protecting group,
P² is selected from a silyl ether protecting group, and
M is selected from a metal cation.

17. The compound according to claim 16, wherein when the compound is represented by formula 6 said P¹ is selected from trimethylsilyl, triethylsilyl, t-butyldimethylsilyl, t-butyldiphenylsilyl, benzyl, p-methoxybenzyl, 3,4-dimethoxy benzyl, methyl ether, t-butyl, trityl, 4,4'-dimethoxytrityl, methoxymethyl, benzyloxymethyl, tetrahydrofuranyl, formyl, chloroacetyl, methoxyacetyl or pivaloyl.

18. The compound according to claim 16, wherein said P² is selected from trimethylsilyl, triethylsilyl, t-butyldimethylsilyl or t-butyldiphenylsilyl.

19. The compound according to claim 16, wherein said M is selected from an alkali metal cation or an alkaline earth metal cation.

20. The compound according to claim 16, which is selected from:

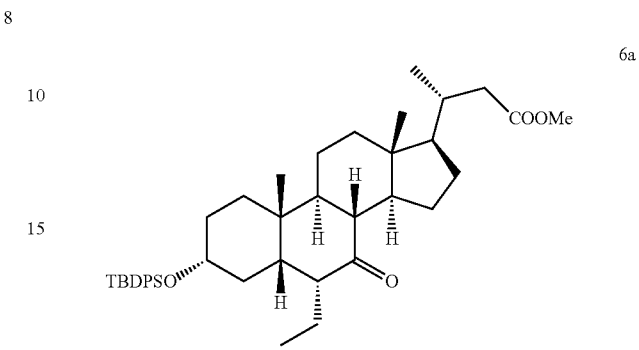

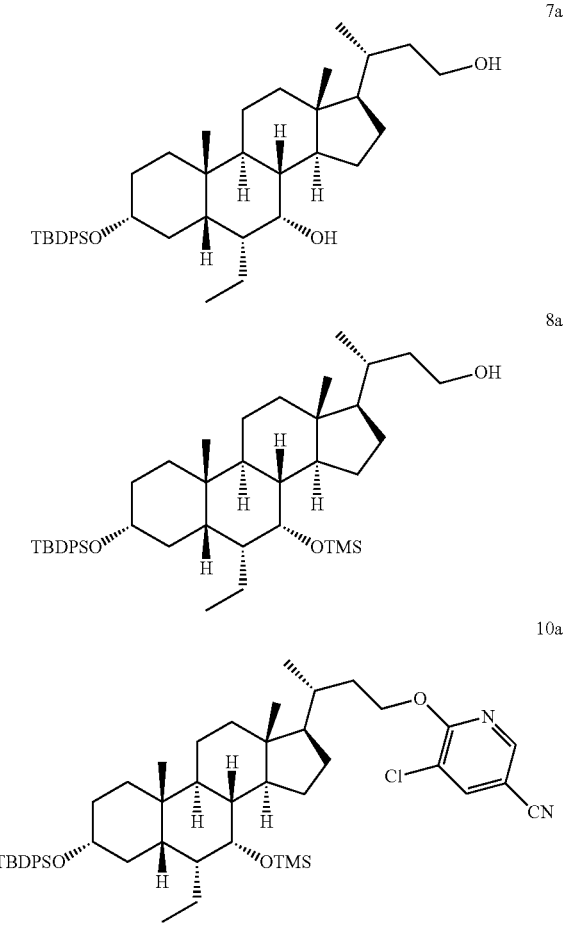

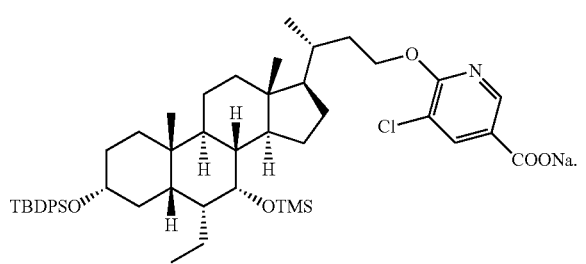

21. The compound according to claim 16, wherein when the compound is represented by formula 7 said $P^1$ is selected from trimethylsilyl, triethylsilyl, t-butyldiphenylsilyl, benzyl, p-methoxybenzyl, 3,4-dimethoxy benzyl, methyl ether, t-butyl, trityl, 4,4'-dimethoxytrityl, methoxymethyl, benzyloxymethyl, tetrahydrofuranyl, formyl, chloroacetyl, methoxyacetyl or pivaloyl.

22. The compound according to claim 16, wherein when the compound is represented by formula 8 said $P^1$ is selected from trimethylsilyl, triethylsilyl, t-butyldiphenylsilyl, benzyl, p-methoxybenzyl, 3,4-dimethoxy benzyl, methyl ether, t-butyl, trityl, 4,4'-dimethoxytrityl, methoxymethyl, benzyloxymethyl, tetrahydrofuranyl, formyl, acetyl, chloroacetyl, methoxyacetyl or pivaloyl.

23. The compound according to claim 16, wherein when the compound is represented by formula 10 or formula 11 said $P^1$ is selected from trimethylsilyl, triethylsilyl, t-butyldimethylsilyl, t-butyldiphenylsilyl, benzyl, p-methoxybenzyl, 3,4-dimethoxy benzyl, methyl ether, t-butyl, trityl, 4,4'-dimethoxytrityl, methoxymethyl, benzyloxymethyl, tetrahydrofuranyl, formyl, acetyl, chloroacetyl, methoxyacetyl or pivaloyl.

\* \* \* \* \*

UNITED STATES PATENT AND TRADEMARK OFFICE
CERTIFICATE OF CORRECTION

PATENT NO. : 11,059,854 B2
APPLICATION NO. : 16/633122
DATED : July 13, 2021
INVENTOR(S) : Li et al.

Page 1 of 1

It is certified that error appears in the above-identified patent and that said Letters Patent is hereby corrected as shown below:

In the Specification

In Column 1, Line 43, delete "Endocrinnol," and insert --Endocrinol,--.

In Column 6, Line 33, delete "(THP)," and insert --(THF),--.

In Column 7, Line 19, delete "KHIVIDS or NaHIVIDS;" and insert --KHMDS or NaHMDS;--.

In Column 8, Line 47, delete "(YEA)," and insert --(TEA),--.

In Column 12, Line 37 (Approx.), delete "(THP)," and insert --(THF),--.

In Column 18, Line 37 (Approx.), delete "dicholomethane" and insert --dichloromethane--.

In Column 22, Lines 22-23, delete "luminescenceamplification" and insert --luminescence amplification--.

In Column 22, Line 45, after "15" insert --µL--.

In Column 24, Line 34 (Approx.), table 2, delete "$c_{max}$" and insert --$C_{max}$--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*